US011752041B2

(12) United States Patent
Robinson et al.

(10) Patent No.: US 11,752,041 B2
(45) Date of Patent: Sep. 12, 2023

(54) SYSTEMS AND METHODS FOR MITIGATING PREMATURE LIGHT DEACTIVATION OF LIGHT DEACTIVATED ADHESIVE DRAPES USING A FILTERING LAYER

(71) Applicant: KCI LICENSING, INC., San Antonio, TX (US)

(72) Inventors: Timothy Mark Robinson, Blandford Forum (GB); Christopher Brian Locke, Bournemouth (GB); Justin Alexander Long, Wimborne (GB)

(73) Assignee: KCI Licensing, Inc., San Antonio, TX (US)

( * ) Notice: Subject to any disclaimer, the term of this patent is extended or adjusted under 35 U.S.C. 154(b) by 218 days.

(21) Appl. No.: 16/644,727

(22) PCT Filed: Sep. 4, 2018

(86) PCT No.: PCT/US2018/049394
§ 371 (c)(1),
(2) Date: Mar. 5, 2020

(87) PCT Pub. No.: WO2019/050858
PCT Pub. Date: Mar. 14, 2019

(65) Prior Publication Data
US 2020/0206036 A1 Jul. 2, 2020

Related U.S. Application Data

(60) Provisional application No. 62/554,307, filed on Sep. 5, 2017.

(51) Int. Cl.
*A61F 13/02* (2006.01)
*A61L 15/58* (2006.01)
*A61L 31/14* (2006.01)

(52) U.S. Cl.
CPC .......... *A61F 13/0253* (2013.01); *A61L 15/58* (2013.01); *A61L 31/14* (2013.01)

(58) Field of Classification Search
CPC ................ A61F 13/00059; A61F 13/14; A61F 13/00017; A61F 13/00029;
(Continued)

(56) References Cited

U.S. PATENT DOCUMENTS 1,355,846 A    10/1920   Rannells
2,539,531 A *   1/1951   Clensos .................. A61K 8/31
                                                      510/157

(Continued)

FOREIGN PATENT DOCUMENTS

AU      550575 B2    3/1986
AU      745271 B2    3/2002
(Continued)

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
(Continued)

*Primary Examiner* — Ophelia A Hawthorne
*Assistant Examiner* — Michael Milo

(57) ABSTRACT

Provided herein is a system and method for mitigating premature light deactivation of light deactivated adhesive drapes. One aspect provides a system comprising a drape, a photosensitive adhesive layer, and a release agent, where the system is adapted to be coupled to a tissue site and released therefrom upon or after exposure to an external stimulus such as certain wavelengths of light. The system may have a filter layer to prevent the photosensitive adhesive from being exposed to deactivation wavelengths prematurely. The filter layer may be printed directly onto the drape and may
(Continued)

be removable after exposure to a solvent, such as isopropyl alcohol (IPA). The filter layer may also be a filter adhesive layer. Another aspect provides a method for application and removal of a drape using by removing one or more of the filter layer and/or the filter adhesive layer and applying light to the drape to deactivate the photosensitive adhesive layer and promote easy, clean, and less painful removal of the drape.

18 Claims, 12 Drawing Sheets

(58) Field of Classification Search
CPC .......... A61F 13/00063; A61F 13/00089; A61F 13/0203; A61F 13/0206; A61F 13/0213; A61F 13/0216; A61F 13/022; A61F 13/0223; A61F 13/0226; A61F 13/00038; A61F 13/025; A61F 13/0253; A61F 2013/00382; A61F 2013/00578; A61F 2013/00719; A61F 2013/00182; A61F 2013/00251; A61F 2013/00255; A61F 2013/0071; A61F 2013/00761; A61F 2013/00774; A61F 2013/00778; A61F 2013/00782; A61F 2013/00804; A61F 2013/00812; A61F 2013/00846; A61F 2013/00863; A61F 2013/00868; A61F 2013/00604; A61F 2013/00412; A61F 2013/00902; A61F 2013/00582; A61F 2013/00685; A61F 2013/00817; A61F 2013/00089; A61F 2013/00361; A61L 15/26; A61L 15/44; A61L 15/58; A61L 2300/404; A61L 31/14; A61M 25/02; A61M 2025/0206; A61M 2025/01213; A61M 2025/0246; A61M 2025/0253; A61M 2025/0266; A61B 46/23
USPC ........ 602/58, 42, 43, 47, 52, 54, 56, 75, 57; 604/180
See application file for complete search history.

(56) References Cited

U.S. PATENT DOCUMENTS

| | | |
|---|---|---|
| 2,547,758 A | 4/1951 | Keeling |
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 8,957,277 B2 * | 2/2015 | Carty ..................... A61L 15/42 602/41 |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0180341 A1 * | 9/2003 | Gooch ................ A61L 26/0066 424/661 |

(56) References Cited

U.S. PATENT DOCUMENTS

| | | | |
|---|---|---|---|
| 2009/0216170 A1* | 8/2009 | Robinson | A61F 13/0246 602/60 |
| 2011/0125187 A1 | 5/2011 | Soltz et al. | |
| 2013/0017246 A1 | 1/2013 | Tunius | |
| 2015/0257938 A1* | 9/2015 | Pensler | A61F 13/0269 602/53 |
| 2017/0189237 A1 | 7/2017 | Locke et al. | |
| 2018/0353640 A1* | 12/2018 | Seibel | C08K 5/0041 |

FOREIGN PATENT DOCUMENTS

| | | | |
|---|---|---|---|
| AU | 755496 B2 | 12/2002 | |
| CA | 2005436 A1 | 6/1990 | |
| CN | 101925369 A | 12/2010 | |
| CN | 103249795 A | 8/2013 | |
| CN | 104204378 A | 12/2014 | |
| DE | 26 40 413 A1 | 3/1978 | |
| DE | 43 06 478 A1 | 9/1994 | |
| DE | 29 504 378 U1 | 9/1995 | |
| DE | 19804665 A1 * | 8/1999 | A61F 13/0223 |
| DE | 10301835 A1 * | 7/2004 | A61F 13/0203 |
| EP | 0100148 A1 | 2/1984 | |
| EP | 0117632 A2 | 9/1984 | |
| EP | 0161865 A2 | 11/1985 | |
| EP | 0358302 A2 | 3/1990 | |
| EP | 1018967 A1 | 7/2000 | |
| GB | 692578 A | 6/1953 | |
| GB | 2195255 A | 4/1988 | |
| GB | 2 197 789 A | 6/1988 | |
| GB | 2 220 357 A | 1/1990 | |
| GB | 2 235 877 A | 3/1991 | |
| GB | 2 329 127 A | 3/1999 | |
| GB | 2 333 965 A | 8/1999 | |
| JP | 4129536 B2 | 8/2008 | |
| JP | 2015221086 A * | 12/2015 | A61F 13/0253 |
| SG | 71559 | 4/2002 | |
| WO | 80/02182 A1 | 10/1980 | |
| WO | 87/04626 A1 | 8/1987 | |
| WO | 90/010424 A1 | 9/1990 | |
| WO | 93/009727 A1 | 5/1993 | |
| WO | 94/20041 A1 | 9/1994 | |
| WO | 96/05873 A1 | 2/1996 | |
| WO | 97/18007 A1 | 5/1997 | |
| WO | 99/13793 A1 | 3/1999 | |
| WO | WO-2015175963 A1 * | 11/2015 | A61F 13/0253 |
| WO | WO-2016/124339 A1 | 8/2016 | |
| WO | WO-2016124339 A1 * | 8/2016 | A61P 17/02 |
| WO | WO-2017031359 A1 * | 2/2017 | B32B 27/06 |

OTHER PUBLICATIONS

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", the Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and ceilified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, an Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: a New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: a Manual of Its Practical Application, (W.B. Saunders Co., Philadelphia, PA 1909), pp. 17-25, 44-64, 90-96, 167-170, and 210-211.

V.A. Solovev et al., Guidelines, the Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

International Search Report and Written Opinion in International Application No. PCT/US2018/049394, dated Jan. 3, 2019.

(56) References Cited

OTHER PUBLICATIONS

Louis C. Argenta, MD and Michael J. Morykwas, PHD; Vacuum-Assisted Closure: a New Method for Wound Control and Treatment: Clinical Experience; Annals of Plastic Surgery; vol. 38, No. 6, Jun. 1997; pp. 563-576.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Chariker, Mark E., M.D., et al; "Effective Management of incisional and cutaneous fistulae with closed suction wound drainage"; Contemporary Surgery, vol. 34, Jun. 1989, pp. 59-63.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A.C. ® Therapy Clinical Guidelines: a Reference Source for Clinicians; Jul. 2007.

* cited by examiner

SYSTEMS AND METHODS FOR MITIGATING PREMATURE LIGHT DEACTIVATION OF LIGHT DEACTIVATED ADHESIVE DRAPES USING A FILTERING LAYER

CROSS-REFERENCE WITH RELATED APPLICATIONS

This application is a national phase application under 35 U.S.C. § 371 of International Application No. PCT/US2018/049394, filed Sep. 4, 2018, which claims the benefit of the U.S. Provisional Application No. 62/554,307, filed Sep. 5, 2017. The contents of the referenced applications are incorporated herein in their entirety.

BACKGROUND

1. Field of Invention

The present application relates generally to the field of tissue treatment, and more specifically to a system and method for facilitating the application and removal of a drape from a tissue site.

2. Description of Related Art

Systems and devices currently exist for the treatment of tissue, such as wound tissue and skin tissue. Some current tissue treatment systems require the use of an adhesive drape to secure all or a portion of the tissue treatment system to a tissue site. For example, an adhesive drape can be used to secure a gauze portion of a bandage to a wound site by adhering to the skin or other tissue surrounding the wound. Drapes intended for use with negative pressure wound therapy (NPWT) have certain desirable characteristics. Some of these characteristics are that the drape is easy to apply, doesn't adhere well to itself if folded (e.g., adhesive to adhesive) upon application to tissue, achieves a good seal with the tissue, adheres well to tissue and to its film (e.g., polyurethane) covering when layered or overlapped, enables atraumatic removal, is highly breathable, is repositionable upon application, and achieves adhesion that is not affected by patient heat or sweat.

SUMMARY

Certain light sensitive or light deactivated adhesive drape systems have been proposed to allow easier removal of the drape system from a patient. The first generation of these light sensitive or light deactivated adhesive drape systems were sensitive to visible light. These drapes were effective at maintaining a seal until they were exposed to visible light. The visible light would deactivate the adhesive tack of the drape system by crosslinking the adhesive so that it irreversibly transformed the adhesive composition from a viscoelastic state to an elastic state. The obvious limitation to this approach was the need for an opaque cover layer to block out the visible light to prevent premature adhesive cross linking and its subsequent deactivation. Unfortunately, these opaque cover layers meant that these drape systems were not particularly transparent for the clinician or nurse to be able to see the wound or periwound area through the dressing. Another iteration of these light deactivated adhesive drape systems has attempted to address this problem using long wavelength UV light to transform/crosslink the adhesive from a viscoelastic state to an elastic state. However, while an opaque cover layer is not necessary in this type of system to block artificial light, the adhesive drape system is not able to be exposed to sunlight due to the UV light spectra within sunlight. This restricts the ability of the patient to go outside, which can be particularly problematic as patients transition from the acute setting to the post-acute setting where they will be more likely to be exposed to UV sunlight.

To alleviate the existing problems with light deactivated adhesive drape systems, the disclosed embodiments describe a light deactivated adhesive drape system having a removable filter layer to protect the light deactivating adhesive drape system from premature deactivation upon inadvertent exposure to deactivation light wavelengths from ambient light. The illustrative embodiments described herein are directed to systems and methods for mitigating premature light deactivation of light deactivated adhesive drapes using a filtering layer.

In some embodiments, a light deactivated adhesive drape system is configured to be coupled to tissue, the system comprising: a drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths, and a flexible film layer; and a removable filter layer configured to block the plurality of light wavelengths that activate the at least one release agent, wherein the plurality of light wavelengths are wavelengths comprising a portion of the visible light spectrum, wherein the filter layer is configured to be removable upon exposure to a solvent. In some embodiments, the solvent is a non-water soluble solvent. In some embodiments, the solvent is isopropyl alcohol (IPA). In some embodiments, the photosensitive adhesive layer comprises an adhesive release layer and one or more of an acrylic and polyurethane adhesive layer. In some embodiments, the adhesive release layer is configured to contact the tissue. In some embodiments, the adhesive release layer is disposed between the tissue and the one or more of an acrylic and polyurethane adhesive layer. In some embodiments, the one or more of an acrylic and polyurethane adhesive layer is disposed between the adhesive release layer and the flexible film layer. In some embodiments, the flexible film layer is disposed between the one or more of an acrylic and polyurethane adhesive layer and the removable filter layer. In some embodiments, the drape further comprises a supporting layer. In some embodiments, the removable filter layer is disposed between the flexible film layer and the supporting layer. In some embodiments, the one or more of an acrylic and polyurethane adhesive layer comprises a thin film. In some embodiments, the one or more of an acrylic and polyurethane adhesive layer comprises a thick gel. In some embodiments, the flexible film layer is a breathable layer. In some embodiments, the flexible film layer is polyurethane. In some embodiments, the removable filter layer is a printed layer disposed directly onto the drape. In some embodiments, the printed layer comprises an IPA soluble, water insoluble polymer and at least one light absorbing dye, an IPA soluble, water insoluble polymer configured to dissolve upon exposure to IPA. In some embodiments, the polymer comprises one or more of polyvinyl acetate (PVAc) or copolymers. In some embodiments, the printed layer comprises a partially-IPA soluble substance and at least one light absorbing dye, the partially-IPA soluble substance configured to soften upon exposure to IPA. In some embodiments, the partially-IPA soluble substance comprises a substance wholly soluble in ketones. In some embodiments, the at least one light absorbing dye comprises one or more of cyanine iodide, alizarin red and yellow, and congo red. In some embodiments, the plurality of light wavelengths includes wavelengths comprising blue through violet portions of the visible light spectrum. In some embodiments, the system further comprises at least one layer of light sensitive ink configured to change color upon exposure to the plurality of light wavelengths that activate the at least one release agent. In some embodiments, the removable filter layer comprises a plurality of pattern coats each configured to block a separate range of the plurality of light wavelengths that activate the at least one release agent, one of the pattern coats being insoluble to IPA. In some embodiments, the pattern coat insoluble to IPA is configured to be peeled off from an outer surface of one or more of the drape and the filter layer. In some embodiments, the removable filter layer comprises a single, opaque layer. In some embodiments, the removable filter layer comprises a single, partially transparent layer. In some embodiments, the system further comprises a filter adhesive layer. In some embodiments, the removable filter layer and the filter adhesive layer comprise a single, combined layer. In some embodiments, the removable filter layer and the filter adhesive layer comprise a single, combined layer.

In some embodiments, a light deactivated adhesive drape system is configured to be coupled to tissue, the system comprising: a drape comprising: a photosensitive adhesive layer having at least one release agent disposed within the adhesive layer, wherein the at least one release agent is configured to weaken a bond of the adhesive layer to the tissue upon exposure to at least one of a plurality of light wavelengths, and a flexible film layer; and a filter adhesive layer, wherein the filter adhesive layer includes at least one colored dye configured to block the plurality of light wavelengths that activate the at least one release agent, wherein the plurality of light wavelengths are wavelengths comprising a portion of the visible light spectrum. In some embodiments, the photosensitive adhesive layer comprises at least one polymer, at least one tackifier, and at least one wetting agent. In some embodiments, the photosensitive adhesive layer is configured to be removed from the tissue with no residue upon exposure to the at least one of the plurality of light wavelengths. In some embodiments, the photosensitive adhesive layer is configured to be peeled off from the tissue.

In some embodiments, a method of making a filter adhesive layer for a light deactivated adhesive drape system configured to be coupled to tissue comprises: mixing together a blend of at least one polymer, at least one tackifier, and at least one wetting agent into one or more of a water-based solution, suspension, or emulsion, and a solvent-based solution, suspension, or emulsion to create an adhesive mix; and mixing the adhesive mix with at least one colored, light absorbing dye. In some embodiments, the at least colored, light absorbing dye comprises one or more of cyanine iodide, alizarin red and yellow, and congo red.

In some embodiments, a method comprises coupling a light deactivated adhesive drape system to a patient's tissue; exposing the photosensitive adhesive layer to the at least one of the plurality of light wavelengths configured to weaken the bond of the adhesive layer; and removing the drape from the tissue. In some embodiments, the method further comprises removing the removable filter layer from the drape system. In some embodiments, removing the removable filter layer from the drape system comprises applying a solvent to the removable filter layer. In some embodiments, the method further comprises wiping away the removable filter layer after applying the solvent to the removable filter layer. In some embodiments, the solvent is IPA. In some embodiments, exposing the photosensitive adhesive layer to the at least one of the plurality of light wavelengths comprises exposing the photosensitive adhesive layer to at least one visible light wavelength. In some embodiments, the one visible light wavelength is in a blue through violet portion of the visible light spectrum.

In some embodiments, a kit comprises: a light deactivated drape system; and at least one wipe containing a solvent configured to remove a removable filter layer. In some embodiments, the drape system and the at least one wipe are sterile.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION

Figure 1A:
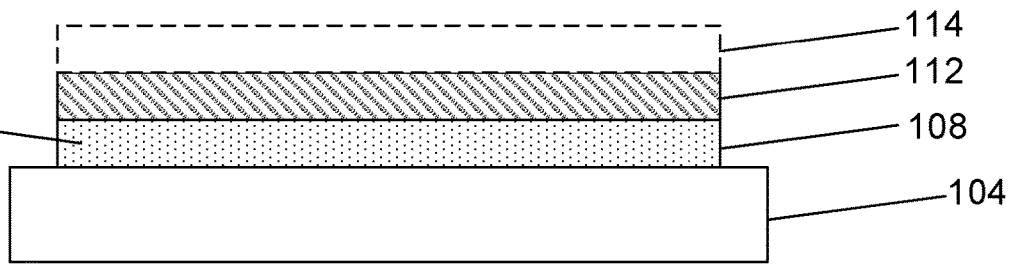
FIGS. 1A-1B are cross-sectional views of a light deactivated adhesive drape system in accordance with an illustrative embodiment of the present disclosure.

In the following detailed description of the preferred embodiments, reference is made to the accompanying drawings that form a part hereof, and in which is shown by way of illustration specific preferred embodiments in which the invention can be practiced. These embodiments are described in sufficient detail to enable those skilled in the art to practice the invention, and it is understood that other embodiments can be utilized and that logical structural, mechanical, electrical, and chemical changes can be made without departing from the spirit or scope of the invention. To avoid detail not necessary to enable those skilled in the art to practice the invention, the description can omit certain information known to those skilled in the art. It is understood that reference to a feature by numeric designation does not necessarily refer only to any particular embodiment depicted in a drawing. The following detailed description is, therefore, not to be taken in a limiting sense, and the scope of the present invention is defined only by the appended claims.

The following definitions are provided to better define the present invention and to guide those of ordinary skill in the art in the practice of the present invention. Unless otherwise noted, terms are to be understood according to conventional usage by those of ordinary skill in the relevant art.

Reduced pressure generally refers to a pressure less than the ambient pressure at a tissue site that is being subjected to treatment. In most cases, this reduced pressure will be less than the atmospheric pressure of the location at which the patient is located. Although the terms "vacuum" and "negative pressure" can be used to describe the pressure applied to the tissue site, the actual pressure applied to the tissue site can be significantly less than the pressure normally associated with a complete vacuum. Consistent with this nomenclature, an increase in reduced pressure or vacuum pressure refers to a relative reduction of absolute pressure, while a decrease in reduced pressure or vacuum pressure refers to a relative increase of absolute pressure.

As used herein, the term "coupled" includes "indirect coupling" via a separate object. For example, a drape can be coupled to the tissue site if both the drape and the tissue site are coupled to one or more third objects, such as a release agent or a second adhesive layer. The term "coupled" also includes "directly coupled," in which case the two objects touch each other in some way. The term "coupled" also encompasses two or more components that are continuous with one another by virtue of each of the components being formed from the same piece of material. Also, the term "coupled" includes chemical coupling, such as via a chemical bond, and electrostatic coupling.

Various aspects of the present invention comprise a system and method for systems and methods for mitigating premature light deactivation of light deactivated adhesive drapes, a portion of which is shown in each of the FIGS. 1A-8. Various embodiments can facilitate the removal of the drape from the tissue site with less trauma to a patient than conventional drapes while preventing premature deactivation of the adhesive. The tissue site may be skin tissue, wound tissue, bone tissue, or any other type of tissue. Various embodiments of the system and method described herein comprise, or can be used with reduced or negative pressure wound healing technology.

Figure 1B:
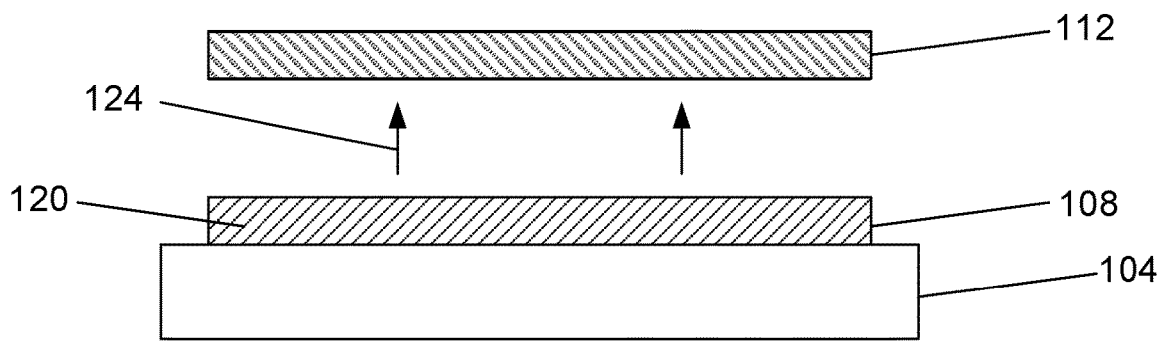

Referring more specifically to FIGS. 1A and 1B, an illustrative embodiment of a light deactivated adhesive drape system 100 disposed onto patient tissue 104 is shown. The system 100 comprises a photosensitive adhesive layer 108 coupled to a flexible film layer 112. In some embodiments, the drape includes both adhesive layer 108 and flexible film layer 112. In the embodiments shown, a drape can be generally understood to be a covering over a tissue 104 that is preferably sterilizable. A drape can comprise a biocompatible thin film material, such as a polymer, a woven or non-woven material, an elastic or non-elastic material, an occlusive or nonocclusive material, and a flexible or inflexible material. A drape can comprise an impermeable, semipermeable, or permeable material. Permeability characteristics can be selected according to desired moisture and gas (e.g., oxygen) transmission. In some embodiments, the drape comprises a material relatively impermeable to moisture and relatively permeable to oxygen. A drape can be coated with a material, for example, to control breathability. A drape can comprise a material which allows or facilitates transmission of external stimuli, such as light, sound, moisture or heat. For example, a drape material can be semi- or substantially transparent to electromagnetic radiation, such as visible, ultraviolet (UV), or infrared light. A drape can be composed of one or more layers. In some embodiments, a drape can be a bilayer drape. For example, a bilayer drape can comprise flexible film layer 112 comprising any biocompatible thin film suitable for tissue or wound contact and a second layer 114 comprising a protective material. As another example, three, four, or more drape layers may be used, with combinations of materials selected according to desired function.

In the embodiment shown, the flexible film layer 112 may be a breathable and/or semiporous film such as polyurethane but other suitable materials may be used. The adhesive layer 108 adheres to the tissue 104 thereby coupling the flexible film layer 112 to the tissue 104. The adhesive layer 108 may cover any portion of the flexible film layer 112 and the tissue 104 as may be required. The adhesive layer 108 can comprise any material, in single or multiple layers, capable of adhering to tissue 104. In some embodiments, prior to the application of a drape to a tissue 104, the adhesive layer 108 can also be covered by an adhesive support layer (not shown). The adhesive support layer can provide rigidity to the drape prior to application and can also aid in the actual application of the drape onto tissue 104. The adhesive support layer can be peeled off or otherwise removed to expose adhesive layer 108 before applying the drape to the tissue. The adhesive layer 108 can comprise one or more materials including, but not limited to, polyurethane, acrylic (e.g., cyanoacrylate), hydrogel, silicon or silicone based material, natural rubber, synthetic rubber, styrene block copolymers, polyvinyl ethers, poly(meth)acrylates, polyolefins, hydrocolloid (e.g., a rubber based hydrocolloid), or a combination thereof. In some embodiments, the adhesive layer 108 comprises a polymer or co-polymer. For example, the adhesive layer 108 can comprise a co-polymer of polyurethane and silicone or various acrylic co-polymers.

The adhesive layer 108 may include at least one release agent 116 comprising a release material. In the embodiment shown, adhesive layer 108 has a plurality of release agents 116 (represented by dots). The release agent 116 can physically or chemically affect adhesion characteristics between a drape and a tissue 104. A release agent 116 can comprise a variety of molecular compositions depending on the particular embodiment being implemented, including but not limited to a photopolymer, an oil particle, a gas particle, a solvent, a lipid, and/or one or more microstructures. Release agents 116 can be present in an inert or inactive form in, on, or near an adhesive layer 108. For example, a release agent 116 can be mixed with the adhesive; on the surface of the adhesive with a random or patterned coverage; coupled to the drape with a random or patterned coverage; or contained within a microstructure located in these or other locations. Upon release or activation, release agents 116 can migrate within the adhesive layer 108 or along an interface between an adhesive layer 108 and a tissue 104 to facilitate the removal of a drape affixed thereto. In the embodiment shown, the release agent 116 is configured to transition from an unreleased state (shown in FIG. 1A) to a release state 120 (represented by diagonal lines in FIG. 1B) to weaken a bond of the adhesive layer 108 to the tissue 104 upon exposure to an external stimulus. Various external stimulus can be employed depending on the particular embodiment being implemented. Non-limiting examples of the external stimulus include electromagnetic (e.g., UV, visible, or infrared light), magnetic, sound, pH, pressure (e.g., positive atmospheric pressure, negative atmospheric pressure, shear force, direct force), thermal, moisture, or a substance. The external stimulus can also be a substance, compound, liquid, or gas capable of reacting with a release agent 116 in adhesive layer 108 such that the release agent 116 transitions from an unreleased state to a released state. In the embodiment shown, the external stimulus is one or more of a plurality of light wavelengths. The weakened bond that occurs as a result of the release of release agent 116 allows a user of the light deactivated adhesive drape system 100 to apply an upward force on flexible film layer 112, such as a force indicated by arrow 124, to remove flexible film layer 112 from tissue 104. The weakened bond reduces the stress applied to tissue 104 in the removal of flexible film layer 112 from tissue 104. Thus, a patient feels less pain and discomfort when the flexible film layer 112 is removed. A residue of molecules from adhesive layer 108 might remain on tissue 104 after removal of flexible film layer 112 depending on a variety of factors such as the type of release agent used.

Referring more specifically to FIG. 1A, in the embodiment shown, release agents 116 are inertly dispersed within adhesive layer 108 and can be located anywhere within adhesive layer 108, as well as any of the outer surfaces of adhesive layer 108, such as an interface between adhesive layer 108 and flexible film layer 112. In some embodiments, release agents 116 can be bonded or coupled directly to flexible film layer 112, and a separate film layer (not shown in FIG. 1A), can separate release agents 116 from adhesive layer 108. In these embodiments, the presence of an external stimulus can weaken, break-down, or increase the permeability of the separate film layer such that release agents 116 are allowed to migrate into adhesive layer 108 to facilitate the removal of flexible film layer 112 from tissue site 105. As shown in FIG. 1B, release agents 116 may be released in the presence of external stimulus such that release agents 116 are allowed to migrate within adhesive layer 108 and the interface between adhesive layer 108 and tissue 104. In the embodiment shown, a UV light source 128 exposes flexible film layer 112 and adhesive 108 to a plurality of light wavelengths 132. In some embodiments, exposure to the plurality of light wavelengths 132 can cause microstructures containing release agents 116 to rupture or tear, thereby releasing release agents 116 from the interior of the microstructures. These released release agents 116 can then be interspersed into adhesive layer 108 and the interface between adhesive layer 108 and tissue 104, thereby weakening the bond between flexible film layer 112 and tissue 104 and facilitating the removal of flexible film layer 112 from tissue 104. As the plurality of light wavelengths 132 reach adhesive 108, release agents 116 may transition from an unreleased state (as shown in FIG. 1A) to a released state 120 (as shown in FIG. 1B) as they are exposed to the plurality of light wavelengths 132. In the embodiment shown, the plurality of light wavelengths 132 are UV wavelengths. In some embodiments, the UV wavelengths may be within a range of 280 nm-380 nm, although it may be preferable to have the UV wavelengths be UVA wavelengths within a range of 315 nm-380 nm.

Referring now to FIGS. 2A-2D, another illustrative embodiment of a light deactivated adhesive drape system 200 disposed onto patient tissue 104 is shown. In this embodiment, light deactivated adhesive drape system 200 is configured to release adhesive layer 108 upon exposure to ambient, visible light instead of UV light. Although having adhesive layer 108 release upon exposure to visible light is advantageous in that it doesn't require a specific UV light source and enables release to occur in any environment having ambient light, it also can increase a likelihood that the adhesive layer 108 will prematurely deactivate. In order to prevent premature deactivation, the adhesive layer 108 may be constructed with release agents 116 that only release upon exposure to certain wavelengths of visible light. For example, in the embodiment shown, release agents 116 will only transition to an unreleased state 120 when exposed to visible light wavelengths in the blue and violet portions of the visible light spectrum. In the embodiment shown, a filter layer 204 is disposed over flexible film layer 112 of the drape. In this embodiment, filter layer 204 is configured to block the visible light wavelengths that release the adhesive layer 108 while allowing other visible light wavelengths to pass through. For example, when exposed to visible light, filter layer 204 will block the blue and violet wavelengths but allow the red, orange, yellow, and/or green wavelengths to pass through. In this way, filter layer 204 is partially transparent and enables a clinician or a nurse to visually inspect the drape and the wound site without premature deactivation of the adhesive layer 108. In some embodiments, filter layer 204 is a colored layer that contains a dye or other coloring agent corresponding to one or more colors of the visible light spectrum that have wavelengths that do not deactivate the adhesive layer 108 (e.g., red, orange, yellow, and/or green).

Figure 2A:
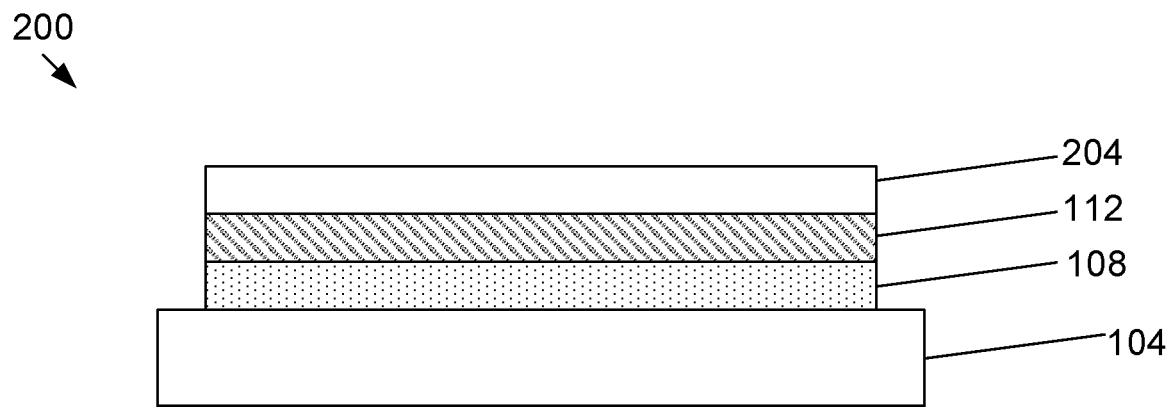
FIGS. 2A-2C are cross-sectional views of a light deactivated adhesive drape system in accordance with another illustrative embodiment of the present disclosure.
Figure 2B:
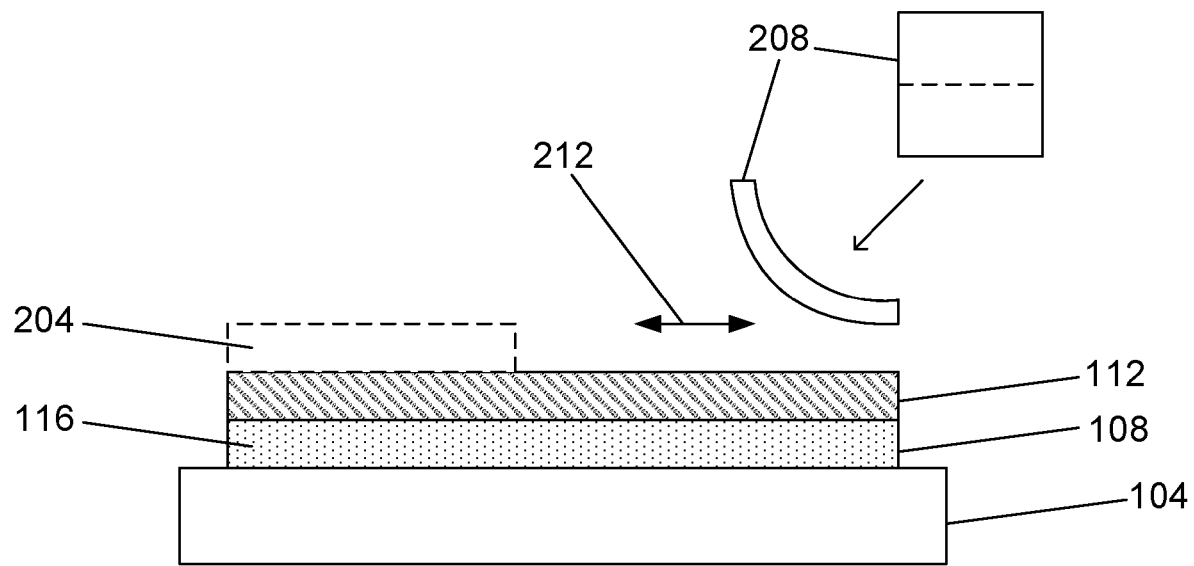
Figure 2C:
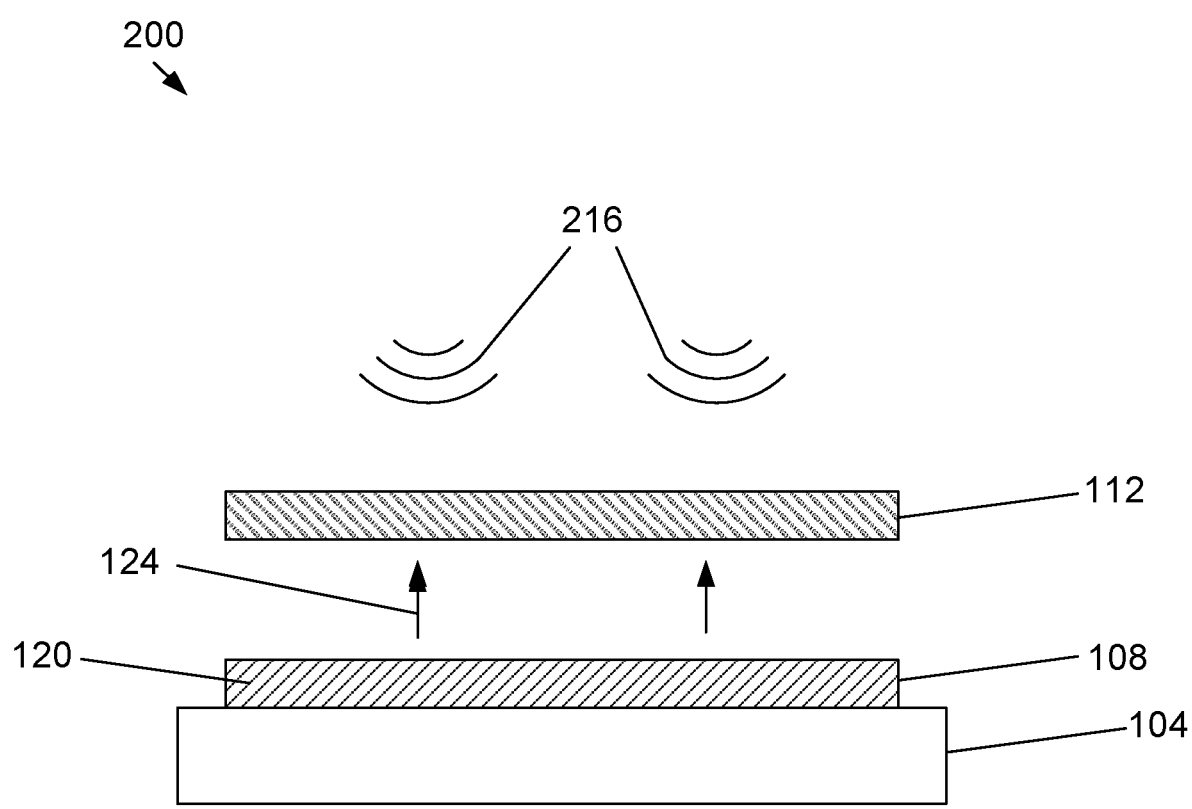

In the embodiment shown in FIG. 2B, filter layer 204 is configured to be removable. This enables the adhesive layer 108 to be deactivated at a time a user desires to remove the drape from tissue 104. In the embodiments shown, the filter layer 204 is a printed layer printed directly onto the drape or the adhesive layer 108. In the embodiment shown in FIG. 2B, the printed layer is soluble in a solvent. The solvent can be a non-water soluble solvent and/or isopropyl alcohol (IPA). After the drape is been applied to tissue 104, the filter layer 204 may be removed with IPA which could be carried in a wipe 208 as is currently in common use for medical purposes. A user can apply the IPA to the surface of the filter layer 204 (e.g., in one or more directions represented by arrows 212. The filter layer 204 will dissolve upon exposure to the IPA. As shown in FIG. 2C, once the filter layer 204 has been removed, the adhesive layer 108 can be exposed to deactivation wavelengths (e.g., ambient light 216) that comprises light wavelengths configured to deactivate adhesive layer 108. Upon exposure to ambient light 216, release agents 116 can transition from an unreleased state to a released state 120. The drape including flexible film layer 112 can then be removed from tissue 104. If any residue of adhesive layer 108 remains on tissue 104 after removal of the drape, it may be removed.

In some embodiments, the printing ink of the printing layer may comprise an IPA soluble (water insoluble) polymer, such as polyvinyl acetate (PVAc) or copolymers. In some embodiments, light absorbing dyes such as single or blends of cyanine iodide; alizarin red and yellow; congo red, can be disposed into the printed layer to absorb the activating wavelengths of release agents 116 disposed in the adhesive layer 108. These could be photo initiators, such as Irgacure 784 (Ciba) activated by light in the blue/green part of the visible light spectrum (i.e., wavelengths in a range of about 450 nm to 550 nm). The printed ink may be further refined to only be softened by IPA instead of completely dissolved. This embodiment could reduce potential mess or spreading of dye from the printed layer beyond the borders of the drape as the remnants of the filter layer 204 would not "bleed" or leach dye after exposure to IPA, but instead become soft and easily removed under a rubbing action (such as that shown by arrows 212) of an IPA wipe 208. In some embodiments, for example, the dye mix disposed in filter layer 204 may be wholly soluble in ketones (e.g., methyl ethyl, ketone, or cellulosic solvent) and swell upon exposure to IPA. In some embodiments, the dye mix disposed in filter layer 204 may contain hydroxyl groups in the polymer or may be one or more types of acrylics.

In some embodiments, one or more light sensitive inks may be applied under the filter layer 204 to indicate exposure to the user by changing color after the desired exposure time has been achieved for deactivation of adhesive layer 108. In some embodiments, the printed filter layer 204 may be applied as a pattern coat and may be used in a number of combinations. For example, two patterns of printed ink can be applied in registration such that only one is removable with solvent. In this embodiment, an attenuated deactivation of the adhesive layer 108 can be achieved since entire adhesive layer 108 does not receive a dose of light upon application of the solvent. This embodiment could enable a single formation adhesive to have a range of release forces depending on the pattern that was applied, and could enable the drape adhesion to be tailored to different patient/wound/therapy requirements.

In some embodiments, printed ink could be applied as a single removable pattern coat and only to some areas of the drape to permit greater drape transparency. In this embodiment, there could possibly be some preliminary adhesive deactivation as light passes through non-printed areas of the adhesive layer 108, but this may be offset by using an adhesive with higher bond strength. In some embodiments, the pattern coat can be applied to the entire drape and can completely block all visible light (i.e., opaque). This embodiment may provide robust protection from deactivation in daylight and could be a simpler and cheaper option to use. In some embodiments, printed ink can be applied as a single removable pattern coat in registration with the light sensitive adhesive layer 108. This could permit greater drape transparency and would limit exposure of the adhesive layer 108 to deactivation light wavelengths, thus preventing premature deactivation. To accommodate any reduction in adhesion due to a drop in adhesive coating coverage, a higher coat weight may be applied, or a stronger adhesive formulation may be used.

Figure 3A:
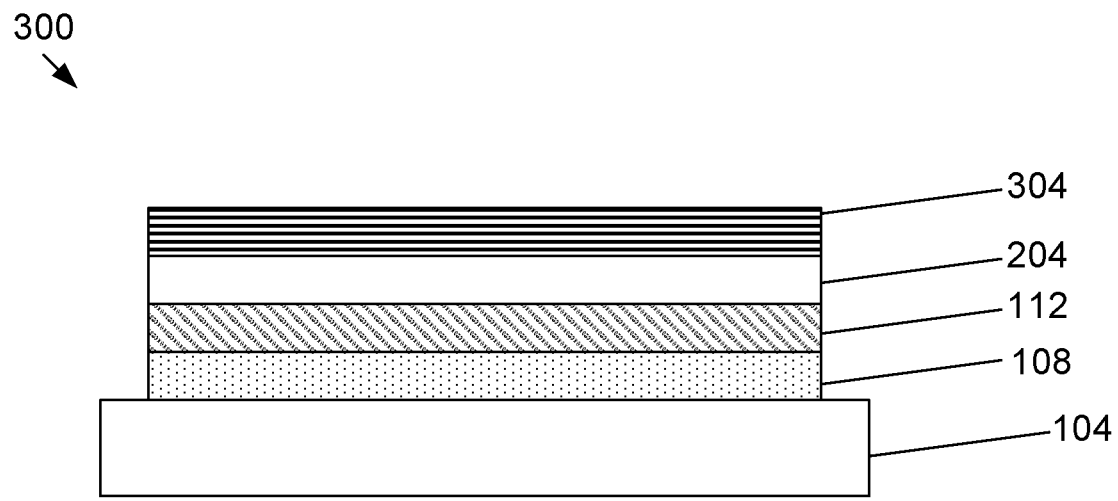
FIGS. 3A-3D are cross-sectional views of a light deactivated adhesive drape system in accordance with another illustrative embodiment of the present disclosure.
Figure 3B:
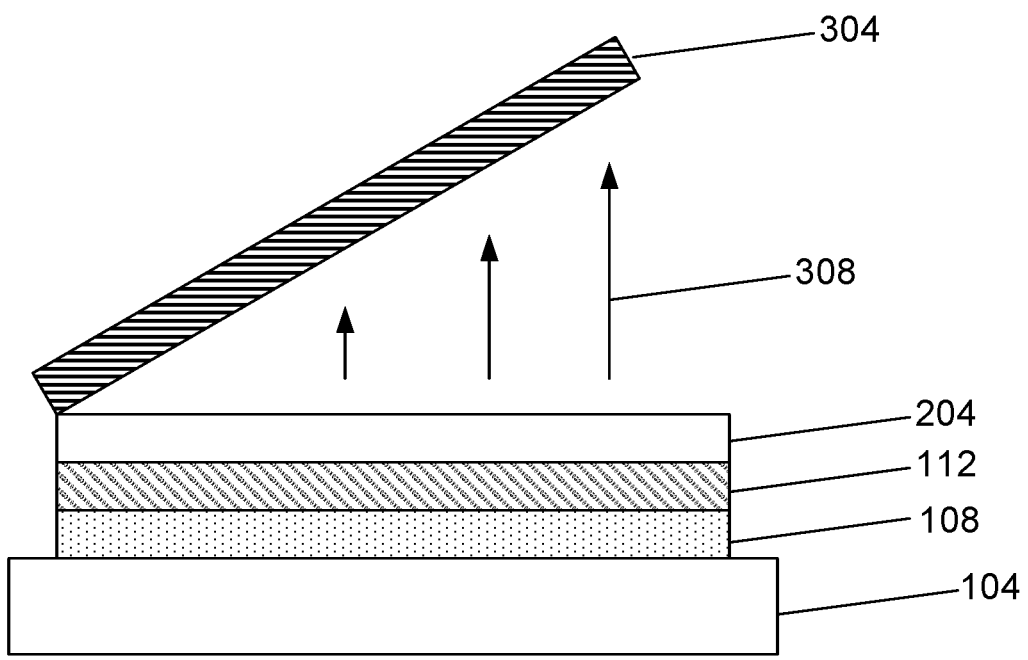
Figure 3C:
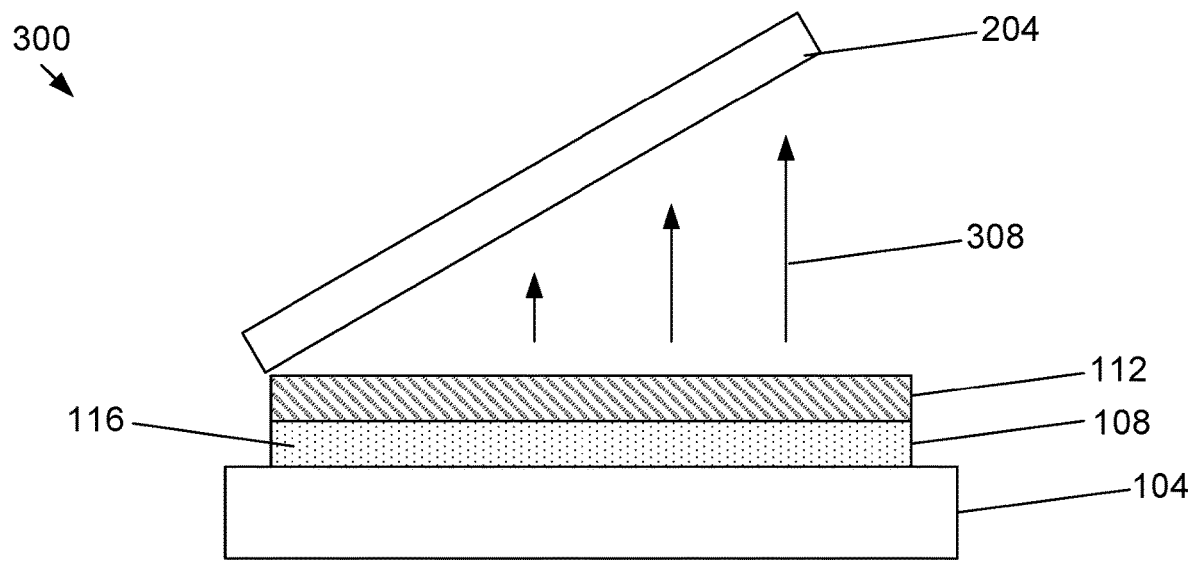
Figure 3D:
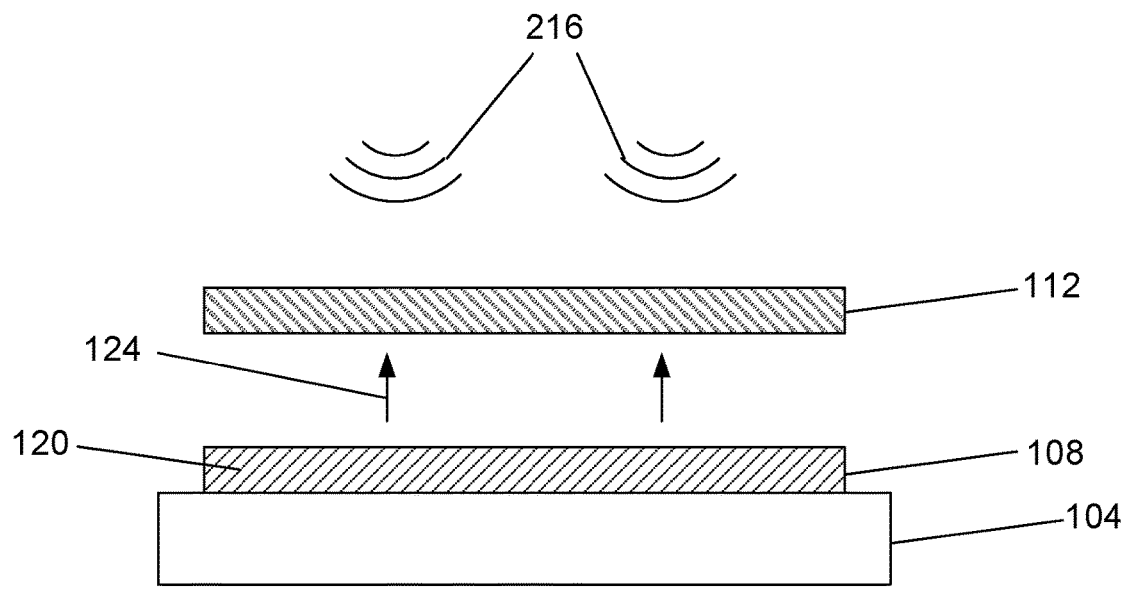

Referring now to FIGS. 3A-3D, another illustrative embodiment of a light deactivated adhesive drape system 300 disposed onto patient tissue 104 is shown. In the embodiment shown, a support layer 304 is provided as part of the drape. The support layer 304 can be removed upon application of the drape to patient tissue 104 or may be removed at a later time (e.g., by providing a force represented by arrows 308, by peeling, and by other suitable methods of removal). After the support layer 304 is removed, filter layer 204 may be exposed and can then be removed at time when deactivation of the adhesive layer 108 is desired. As shown in FIG. 3C, upon removal of the support layer 304, filter layer 204 can be removed from flexible film layer 112 using an upward or other directional force represented by arrows 308. As shown in FIG. 3D, upon removal of the support layer 304 and filter layer 204, adhesive layer 108 can be exposed to ambient, visible light 216 that comprises light wavelengths configured to deactivate adhesive layer 108 (e.g., blue and/or violet wavelengths). Upon exposure to ambient light 216, release agents 116 can transition from an unreleased state to a released state 120 and the drape including flexible film layer 112 can be removed from tissue 104.

Referring now to FIGS. 4A-4D, another illustrative embodiment of a light deactivated adhesive drape system 400 disposed onto patient tissue 104 is shown. Similar to previous embodiments, a removable support layer 404 can be provided. In the embodiment shown, a transparent flexible layer 408 may be provided over a filter adhesive layer 412. In some embodiments, transparent flexible layer 408 is a breathable layer (i.e., at least semi porous layer). In some embodiments, filter adhesive layer 412 can be made of various standard adhesives such as a blend of polymers (e.g., acrylics or polyurethanes), tackifiers, and wetting agents. In some embodiments, filter adhesive layer 412 can be applied to the drape as a hot melt (i.e., no/low solvent) water or solvent based solution, or a suspension, or an emulsion. Adhesive ingredients in filter adhesive layer 412 can be added to various mixing vessels and mixed with one or more colored dyes configured to block certain light wavelengths that deactivate adhesive layer 108. Some examples of these colored dyes are cyanine iodide, alizarin red and yellow, and congo red.

Figure 4A:
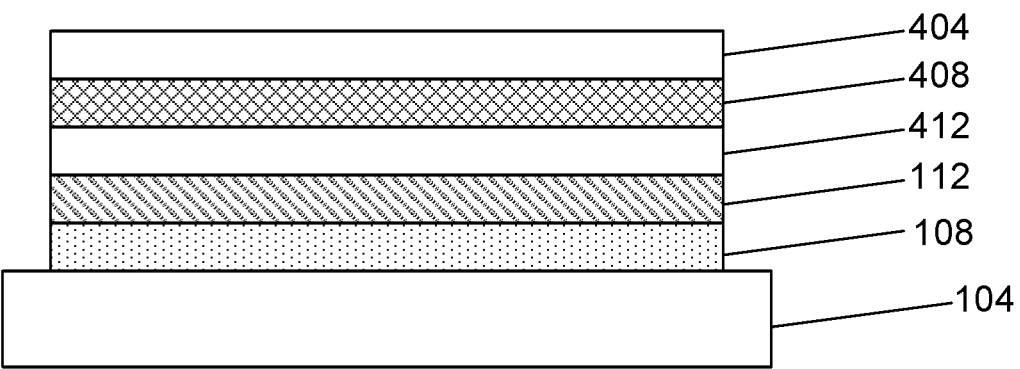
FIGS. 4A-4D are cross-sectional views of a light deactivated adhesive drape system in accordance with another illustrative embodiment of the present disclosure.
Figure 4B:
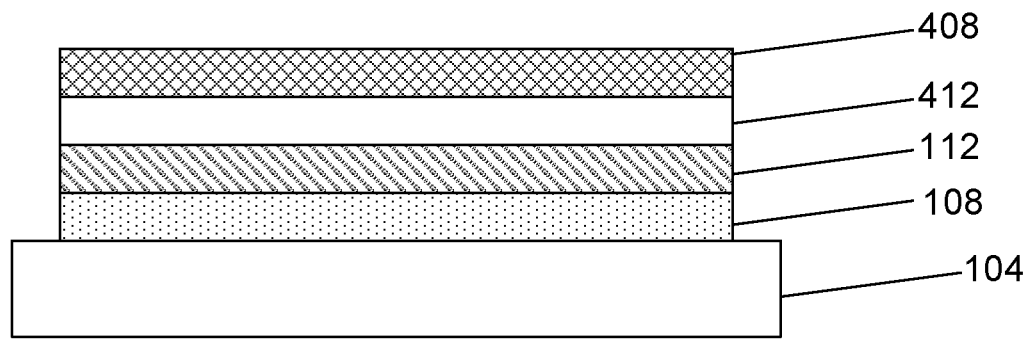
Figure 4C:
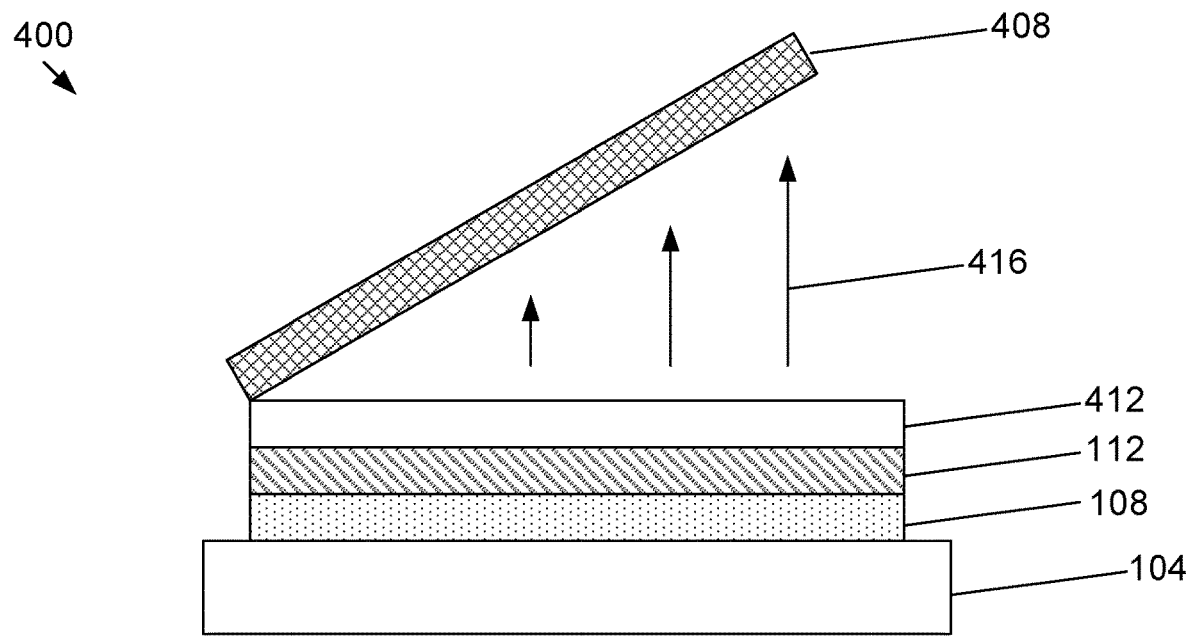
Figure 4D:
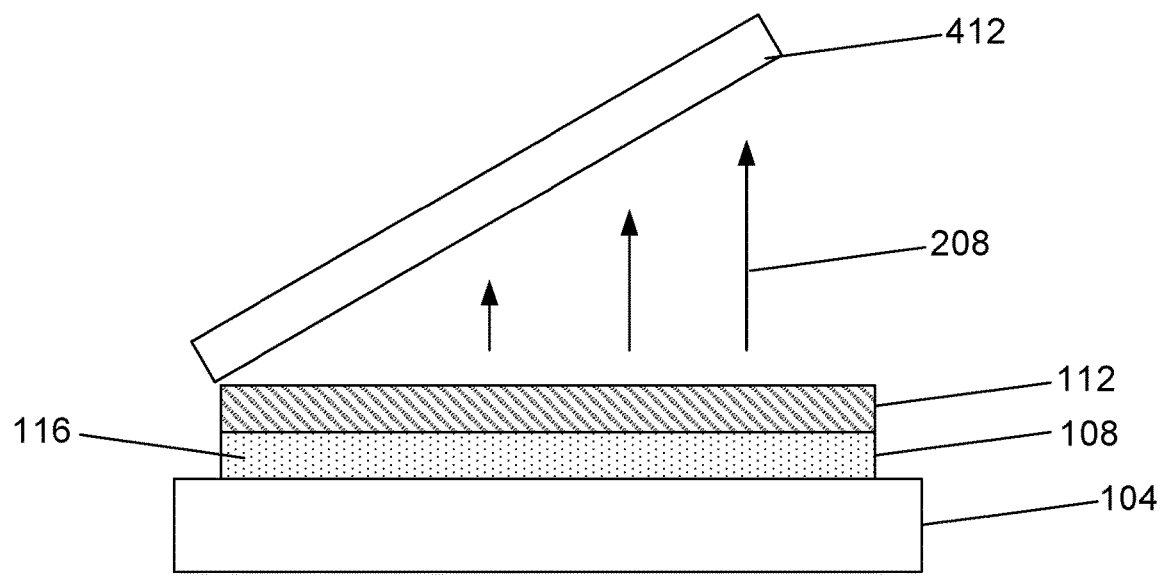

Transparent flexible layer 408 and filter adhesive layer 412 can be removed at a time when deactivation of the adhesive layer 108 is desired. As shown in FIGS. 4C and 4D, upon removal of the transparent flexible layer 408, filter adhesive layer 412 can be removed from flexible film layer 112 using an upward or other directional force represented by arrows 308. Upon removal of the transparent flexible layer 408 and filter adhesive layer 412, adhesive layer 108 can be exposed to ambient, visible light 216 that comprises light wavelengths configured to deactivate adhesive layer 108 (e.g., blue and/or violet wavelengths). Upon exposure to ambient light 216, release agents 116 can transition from an unreleased state to a released state 120 and the drape including flexible film layer 112 can be removed from tissue 104.

Figure 5:
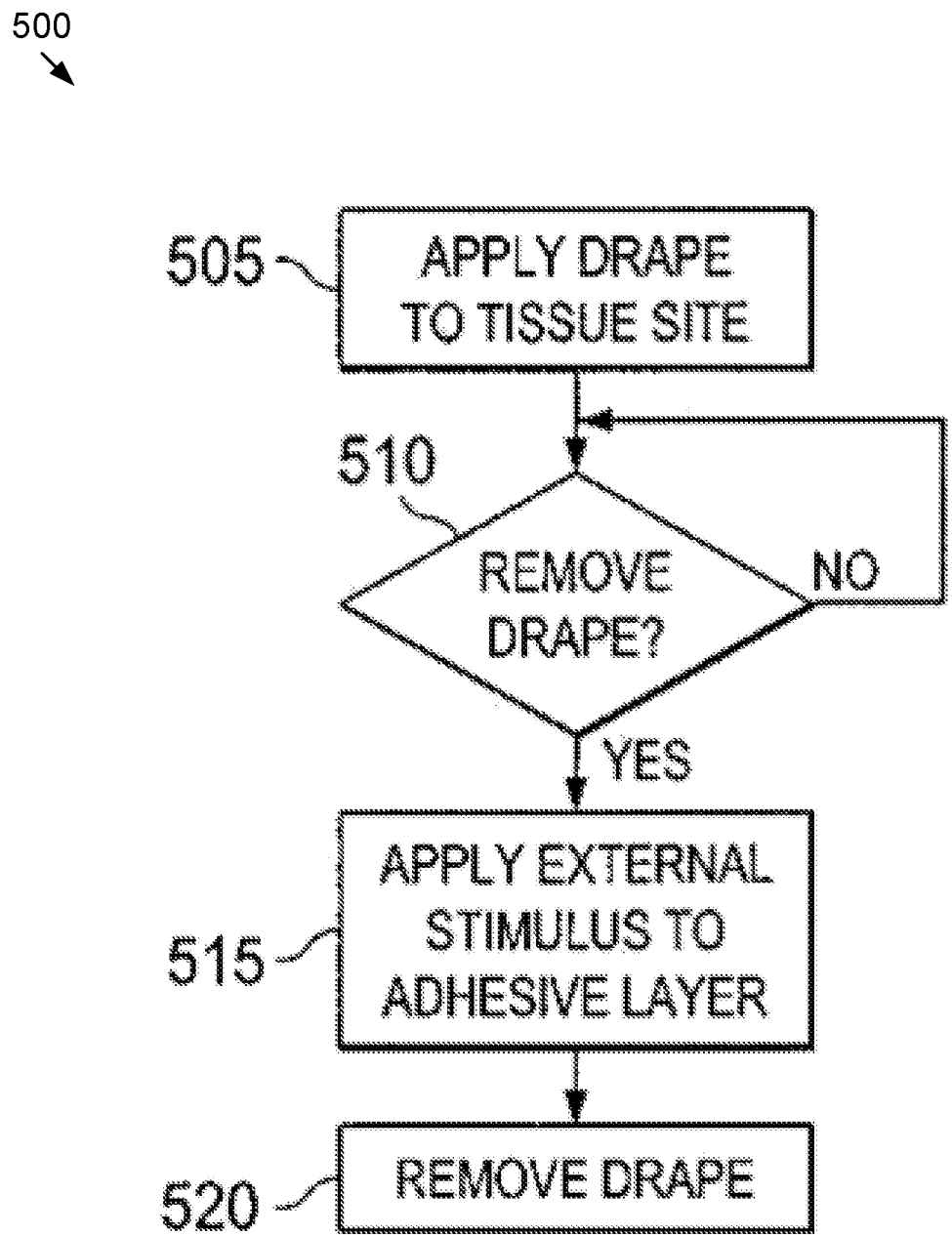
FIG. 5 is a flowchart illustrating a process for using a light deactivated adhesive drape system in accordance with an illustrative embodiment of the present disclosure.

FIG. 5 depicts a flowchart illustrating a general process 500 for facilitating removal of a light deactivated adhesive drape system from a tissue 104 in accordance with an illustrative embodiment of the disclosure. The process illustrated in FIG. 5 can be implemented by a user of a reduced or negative pressure treatment system. The process begins by applying a drape to a tissue 104 (step 505). In this step, adhesive layer 108 can bind to the tissue 104. Also in this step, reduced or negative pressure can be applied to the tissue 104 using a reduced or negative pressure treatment system. The process determines whether to remove the drape from the tissue 104 (step 510). If the process determines not to remove the drape from the tissue 104, the process returns to step 510. If the process determines to remove the drape from the tissue 104, the process applies an external stimulus to the drape, including the adhesive layer 108 coupled to the drape (step 515). In this step, a release agent 116 can be released in accordance with any of the illustrative embodiments described above to facilitate the removal of the drape from the tissue 104. The process then removes the drape from the tissue 104 (step 520).

Figure 6:
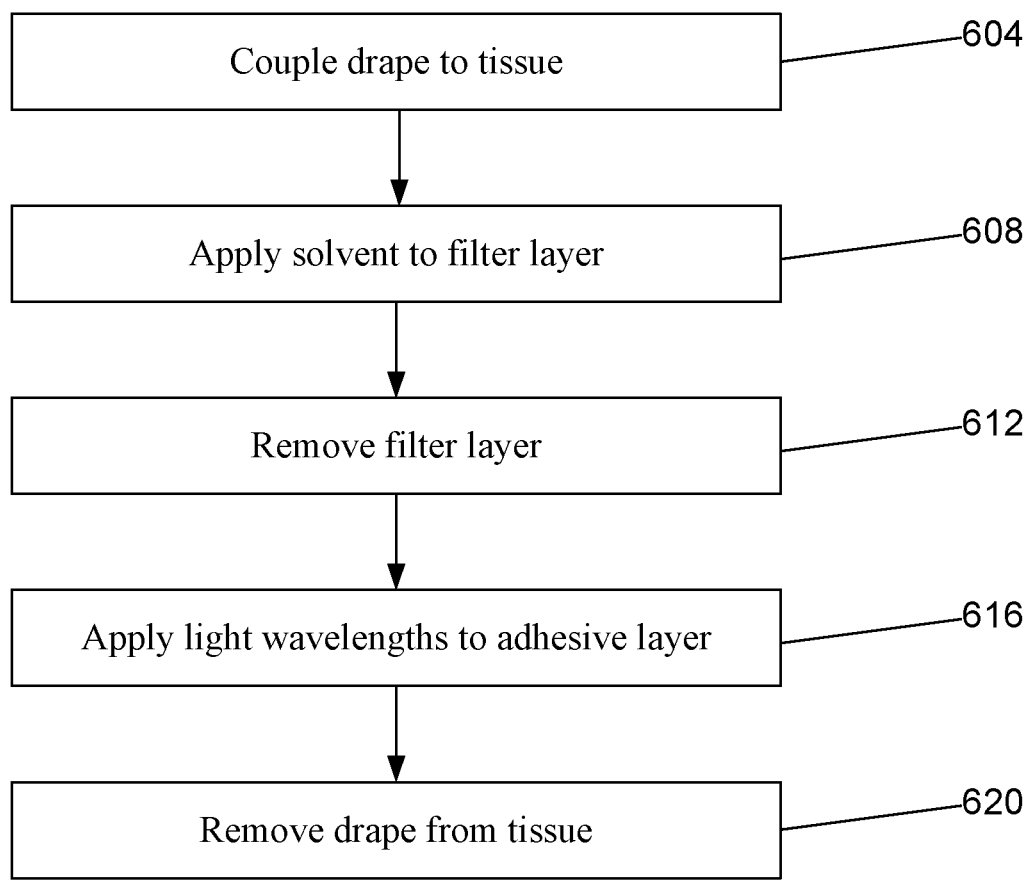
FIG. 6 is a flowchart illustrating a process for using a light deactivated adhesive drape system in accordance with another illustrative embodiment of the present disclosure.

FIGS. 6-9 depict flowcharts illustrating processes 600, 700, 800, 900 for facilitating removal of a light deactivated adhesive drape system from a tissue 104 in accordance with an illustrative embodiment of the disclosure. Referring to FIG. 6, process 600 begins by coupling a drape to a tissue (step 604). In this embodiment, the drape may have a printed filter layer that is reactive to a solvent. Process 600 continues by, when the drape is desired to be removed, the solvent is applied to the printed filter layer, causing the printed filter layer to dissolve or soften (step 608). Process 600 continues by removing the printed filter layer (step 612) and applying certain deactivating light wavelengths to the photosensitive adhesive layer to deactivate the adhesive (step 612). The process then enables a removal of the drape from the tissue (step 616).

Figure 7:
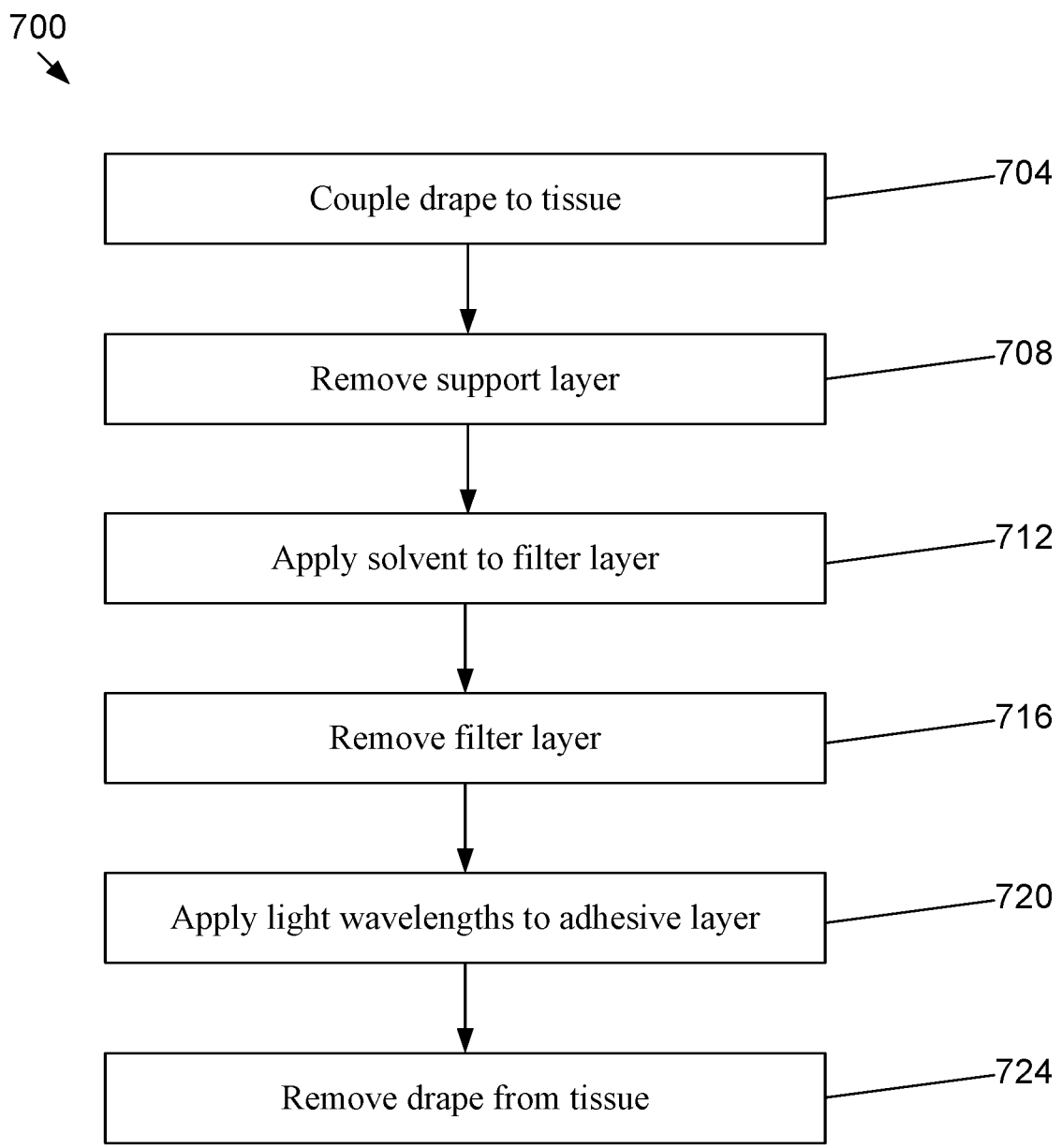
FIG. 7 is a flowchart illustrating a process for using a light deactivated adhesive drape system in accordance with another illustrative embodiment of the present disclosure.

Referring to FIG. 7, process 700 begins by coupling a drape to a tissue 104 (step 704). In this embodiment, the drape may have a support layer 304 coupled to the drape similar to the embodiments shown in FIGS. 3A-3B. Process 700 continues by, when the drape is desired to be removed, the solvent is applied to the printed filter layer, causing the printed filter layer to dissolve or soften (step 712). Process 700 continues by removing the printed filter layer (step 716) and applying certain deactivating light wavelengths to the photosensitive adhesive layer to deactivate the adhesive (step 720). The process then enables a removal of the drape from the tissue (step 724).

Figure 8:
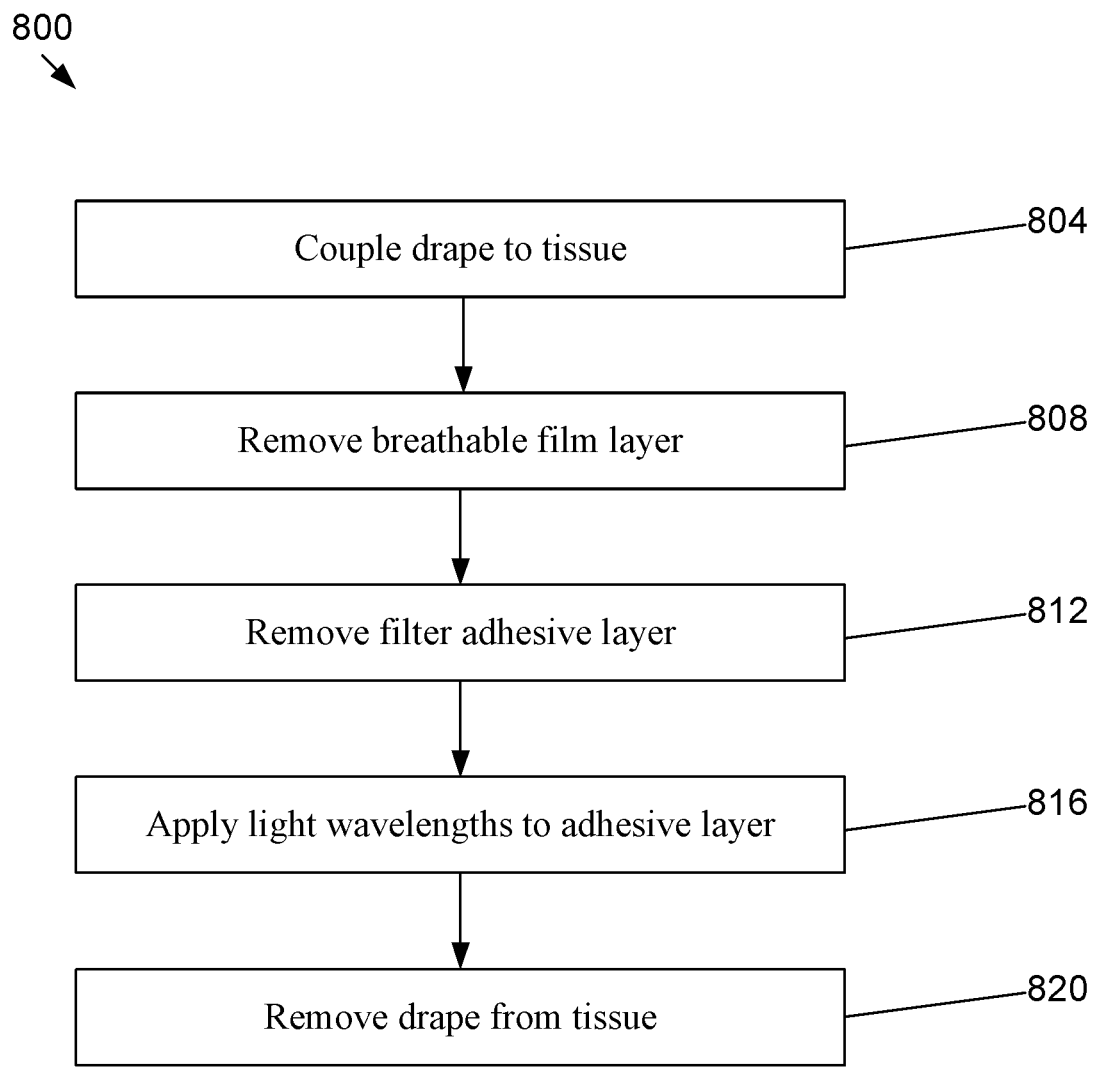
FIG. 8 is a flowchart illustrating a process for using a light deactivated adhesive drape system in accordance with another illustrative embodiment of the present disclosure.

Referring to FIG. 8, process 800 begins by coupling a drape to a tissue 104 (step 804). In this embodiment, the drape may have a transparent flexible layer 404 that is breathable and a filter adhesive layer 408 coupled to the drape similar to the embodiments shown in FIGS. 4A-4D. Process 800 continues by removing the transparent flexible layer (step 808) and the filter adhesive layer (step 812) and applying certain deactivating light wavelengths to the photosensitive adhesive layer to deactivate the adhesive (step 816). The process then enables a removal of the drape from the tissue (step 820).

Figure 9:
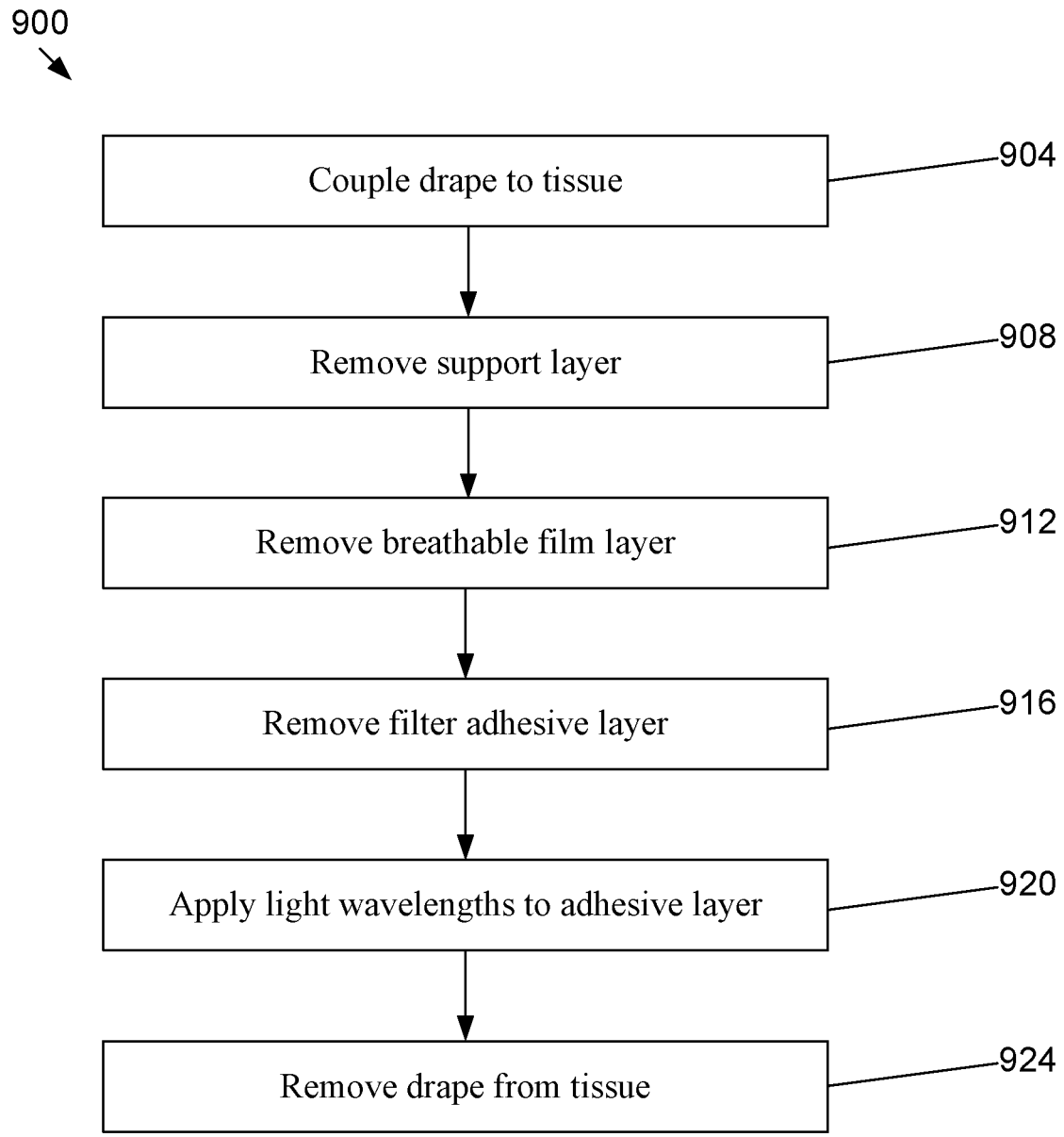
FIG. 9 is a flowchart illustrating a process for using a light deactivated adhesive drape system in accordance with another illustrative embodiment of the present disclosure.

Referring to FIG. 9, process 800 begins by coupling a drape to a tissue 104 (step 904). In this embodiment, the drape may have a support layer 304, a transparent flexible layer 404 that is breathable and a filter adhesive layer 408 coupled to the drape. Process 900 continues by removing the support layer (step 908), the transparent flexible layer (step 912), and the filter adhesive layer (step 916) and applying certain deactivating light wavelengths to the photosensitive adhesive layer to deactivate the adhesive (step 920). The process then enables a removal of the drape from the tissue (step 924).

The flowcharts and block diagrams in the different depicted embodiments illustrate the architecture, functionality, and operation of some possible implementations of the apparatus and methods. In some alternative implementations, the function or functions noted in the block can occur out of the order noted in the figures. For example, in some cases, two blocks shown in succession can be executed substantially concurrently, or the blocks can sometimes be executed in the reverse order, depending upon the functionality involved.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A light deactivated adhesive drape system configured to be coupled to tissue, the system comprising:
   a drape comprising:
      a photosensitive adhesive layer comprising an adhesive release layer and one or more of an acrylic or polyurethane adhesive layer, the photosensitive adhesive layer having at least one release agent disposed within the photosensitive adhesive layer, wherein the at least one release agent is configured to weaken a bond of the photosensitive adhesive layer to the tissue upon exposure to at least one of a plurality of light wavelengths, the plurality of light wavelengths comprising a portion of a visible light spectrum;
      a flexible film layer coupled to the photosensitive adhesive layer; and
      a removable filter layer coupled to the flexible film layer opposite the photosensitive adhesive layer, the removable filter layer being a partially transparent colored layer that includes at least one light absorbing dye corresponding to one or more colors of the visible light spectrum, the one or more colors of the visible light spectrum having wavelengths different from the plurality of light wavelengths that activate the at least one release agent,
      wherein the removable filter layer is configured to block the plurality of light wavelengths that activate the at least one release agent and be removable upon exposure to a solvent.

2. The system of claim 1, wherein the removable filter layer is a printed layer disposed directly onto the drape, and wherein the plurality of light wavelengths includes wavelengths comprising blue through violet portions of the visible light spectrum.

3. The system of claim 2, wherein the printed layer comprises an isopropyl alcohol (IPA) soluble, water insoluble polymer and wherein the polymer comprises one or more of polyvinyl acetate (PVAc) or copolymers.

4. The system of claim 2, wherein the printed layer comprises a partially-isopropyl alcohol (IPA) soluble substance and the at least one light absorbing dye comprises one or more of cyanine iodide, alizarin red and yellow, and congo red, the partially—IPA soluble substance configured to soften upon exposure to IPA, and wherein the partially IPA soluble substance comprises a substance wholly soluble in ketones.

5. The system of claim 1, wherein the adhesive release layer is configured to contact the tissue, wherein the adhesive release layer is disposed between the tissue and the one or more of the acrylic and the polyurethane adhesive layer, and wherein the one or more of the acrylic and the polyurethane adhesive layer is disposed between the adhesive release layer and the flexible film layer.

6. The system of any of claim 5, wherein the flexible film layer is disposed between the one or more of the acrylic and the polyurethane adhesive layer and the removable filter layer, wherein the drape further comprises a supporting layer, and wherein the removable filter layer is disposed between the flexible film layer and the supporting layer.

7. The system of claim 1, wherein the solvent is a non-water soluble solvent or wherein the solvent is isopropyl alcohol (IPA), and wherein the flexible film layer is a breathable layer or polyurethane.

8. The system of claim 1, wherein the one or more of the acrylic and the polyurethane adhesive layer comprises a thin film or a thick gel.

9. The system of claim 1, further comprising at least one layer of light sensitive ink configured to change color upon exposure to the plurality of light wavelengths that activate the at least one release agent, wherein the removable filter layer comprises a plurality of pattern coats each configured to block a separate range of the plurality of light wavelengths that activate the at least one release agent, wherein at least one of the plurality of pattern coats is insoluble to isopropyl alcohol (IPA), and wherein the at least one of the plurality of pattern coats insoluble to IPA is configured to be peeled off from an outer surface of one or more of the drape and the removable filter layer.

10. The system of any of claim 1, wherein the removable filter layer further comprises a filter adhesive layer, wherein the removable filter layer and the filter adhesive layer comprise a single, combined layer.

11. A kit comprising:
a drape system, wherein the drape system comprises:
  a drape comprising:
    a photosensitive adhesive layer comprising an adhesive release layer and one or more of an acrylic or polyurethane adhesive layer, the photosensitive adhesive layer having at least one release agent disposed within the photosensitive adhesive layer, wherein the at least one release agent is configured to weaken a bond of the photosensitive adhesive layer to tissue upon exposure to at least one of a plurality of light wavelengths, the plurality of light wavelengths comprising a portion of a visible light spectrum;
    a flexible film layer coupled to the photosensitive adhesive layer; and
    a removable filter layer coupled to the flexible film layer opposite the photosensitive adhesive layer, the removable filter layer being a partially transparent colored layer that includes at least one light absorbing dye corresponding to one or more colors of the visible light spectrum, the one or more colors of the visible light spectrum having wavelengths different from the plurality of light wavelengths that activate the at least one release agent, and wherein the removable filter layer is configured to block the plurality of light wavelengths that activate the at least one release agent and be removable upon exposure to a solvent; and
at least one wipe containing the solvent.

12. The kit of claim 11, wherein the polyurethane adhesive layer is disposed between the adhesive release layer and the flexible film layer.

13. The kit of claim 12, wherein the flexible film layer is a printed layer.

14. The kit of claim 11, wherein the drape system and the at least one wipe are sterile.

15. The kit of claim 11, wherein the solvent is isopropyl alcohol (IPA).

16. A method comprising:
coupling a light deactivated adhesive drape system to a patient's tissue, wherein the light deactivated adhesive drape system comprises: a drape comprising:
  a photosensitive adhesive layer comprising an adhesive release layer and one or more of an acrylic or polyurethane adhesive layer, the photosensitive adhesive layer having at least one release agent disposed within the photosensitive adhesive layer, wherein the at least one release agent is configured to weaken a bond of the photosensitive adhesive layer to the tissue upon exposure to at least one of a plurality of light wavelengths, the plurality of light wavelengths comprising a portion of a visible light spectrum;
  a flexible film layer film layer coupled to the photosensitive adhesive layer opposite the tissue; and
  a removable filter layer coupled to the flexible film layer opposite the photosensitive adhesive layer, the removable filter layer being a partially transparent colored layer that includes at least one light absorbing dye corresponding to one or more colors of the visible light spectrum, the one or more colors of the visible light spectrum having wavelengths different from the plurality of light wavelengths that activate the at least one release agent, wherein the removable filter layer is configured to block the plurality of light wavelengths that activate the at least one release agent and be removable upon exposure to a solvent;
exposing the photosensitive adhesive layer to the at least one of the plurality of light wavelengths configured to weaken the bond of the photosensitive adhesive layer; and
removing the drape from the tissue.

17. The method of claim 16, further comprising:
removing the removable filter layer from the drape system, wherein removing the removable filter layer from the drape system comprises applying the solvent to the removable filter layer; and
after applying the solvent to the removable filter layer, wiping away the removable filter layer.

18. The method of claim 16, wherein exposing the photosensitive adhesive layer to the at least one of the plurality of light wavelengths comprises exposing the photosensitive adhesive layer to at least one visible light wavelength, and wherein the at least one of the plurality of light wavelengths is in a blue through violet portion of the visible light spectrum.

* * * * *